United States Patent [19]

Chung et al.

[11] Patent Number: 5,659,130
[45] Date of Patent: Aug. 19, 1997

[54] SIMPLE DEVICE FOR TESTING CHEMICAL PERMEATION

[75] Inventors: Yueh-Wen Chung; Hsieh-Chang Chang; Tsuey-Huah Hwang; Yih-Shiaw Huang; C. H. Lo, all of Hsinchu Hsien, Taiwan

[73] Assignee: Industrual Technology Research Institute, Hsinchu, Taiwan

[21] Appl. No.: 626,829

[22] Filed: Apr. 3, 1996

[51] Int. Cl.[6] .......................... G01N 13/04; G01N 15/08; C12Q 1/70

[52] U.S. Cl. ..................... 73/64.47; 73/38; 73/64.55; 436/5; 422/101

[58] Field of Search .................... 73/38, 64.54, 64.55, 73/61.73, 64.47; 436/5, 6; 422/101

[56] References Cited

U.S. PATENT DOCUMENTS

| | | | |
|---|---|---|---|
| 4,455,864 | 6/1984 | Wallner | 73/64.3 |
| 4,594,884 | 6/1986 | Bondi et al. | 73/64.3 |
| 4,771,004 | 9/1988 | Higuchi | 436/5 |
| 4,863,696 | 9/1989 | Saydek et al. | 422/101 |
| 5,005,403 | 4/1991 | Steudle et al. | 73/64.3 |
| 5,141,873 | 8/1992 | Steudle | 436/148 |
| 5,266,495 | 11/1993 | Lapidus | 436/63 |
| 5,361,625 | 11/1994 | Ylvisaker | 73/38 |
| 5,411,888 | 5/1995 | Gordon et al. | 436/5 |
| 5,422,240 | 6/1995 | Lytte et al. | 435/5 |
| 5,483,078 | 1/1996 | Hermann et al. | 250/559.32 |

*Primary Examiner*—Hezron E. Williams
*Assistant Examiner*—J. David Wiggins
*Attorney, Agent, or Firm*—W. Wayne Liauh

[57] ABSTRACT

A simple test device for protection against chemical permeation is disclosed. It includes a test chamber, a solvent sample cup, upper and lower fixing plates, upper and lower gaskets, an air filtering apparatus, a gas diffusing pan and a number of screws. By means of a sensor and related control circuit, the permeation time of gloves and protection wears in a specific solvent is indicated.

4 Claims, 8 Drawing Sheets

FIG. 3

(PRIOR ART)

SIMPLE DEVICE FOR TESTING CHEMICAL PERMEATION

BACKGROUND OF THE INVENTION

In general, for operators who are exposed to an environment filled with chemicals, the skin contact is an additional path of hazardous exposure other than breathing which permits chemical media to penetrate human bodies. It has been reported that about 40% of vocational diseases are related to skin syndromes. Gloves and protection wears are the prime protection instruments. It is very difficult to prevent hand from touching chemicals during work in plants or laboratories where various chemicals are held. Sometimes workers are required to grasp and merge un-finished products into solvent while wearing gloves when automated manufacturing equipment is unavailable. In such a case, the information about the solubility of the glove material in a specific solvent and the expiration of effective protection should be known. Generally, some test information, e.g., breakthrough time, permeation rate, and suitability in a specific solvent, are listed in a portion of the glove and wears. However some products lack the test information or are not included in a list of chemicals that show the compatibility to solvents and the expiration time of those gloves for multi-chemical media applications. It is not practical in terms of the cost and technical difficulties to have a complicated testing facility in the working positions or laboratories to test the solubility of gloves in the applied solvent.

Figure 1:
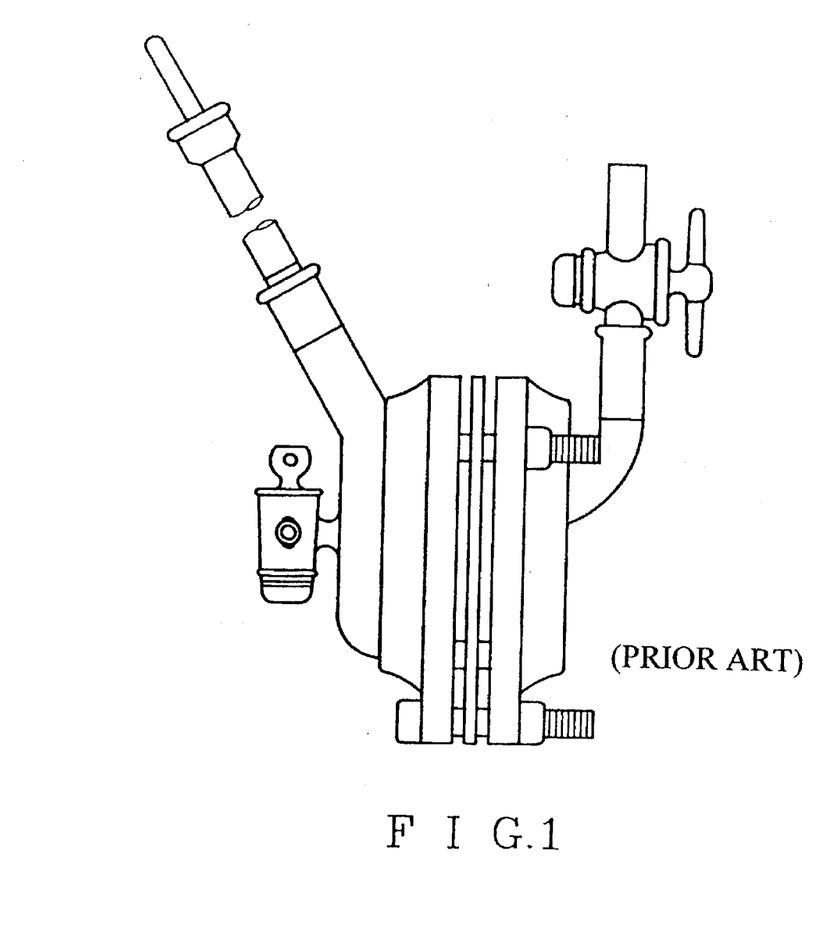
FIG. 1 is a side view of an ordinary permeation test chamber.

A generally utilized technique is shown in FIG. 1, which indicates the side view of a permeation test chamber. This technique was published in the ASTM yearbook as "The Standard Testing Approach for Permeation Resistance of Material for Protection Wears Against Liquid or Gas under Continuous Contact," and with a designation code of F739. The first figure in this report is a sealed test chamber (as shown in FIG. 1), which was fixed by screws. When it is in use, the chamber was erected which resulted in an uneven permeation for the tested specimen. The permeation rate is faster on the bottom than on the top, because the solvent is likely to be more concentrated on the lower portion of the chamber. Thereof, it would also cause leakage of solvent in the connection regions of the chamber. Furthermore, the aforesaid method merely illustrates the test chamber without clarifying the measurement of testing time. According to some literature, if the test method is different, the permeation time cannot be compared.

SUMMARY OF THE INVENTION

The primary objective of the present invention is to provide a kind of device suited for operation in working areas to monitor the extent of chemical permeations in gloves or protection wears from specific solutions. When the concentration of the permeated solvent reached a predetermined value, a warning signal is sent out to inform the user about the service life of the gloves or protection wears under a specific working condition. When the device of the present invention is used to test gloves or protection wears, the tested specimens and solvent are installed by following the operation procedures. No additional instruments or recorders are required to indicate the permeation time since it is automatically displayed by this device. The deviation between the tested results from the presently invented device and from the ASTM method is less than 20%.

The structure of the present invention mainly comprises a test chamber, a sample cup for test solvent, upper and lower fixing plates, upper and lower gaskets, an air filtering apparatus, a gas diffusing pan, and a plurality of screws. Since this invented device is perfectly sealed and appropriately constructed, it provides reliable test results. In addition, it indicates the permeation time of a specific solvent to protection gloves, garment or skin coveting articles and other personal barrier wears by means of its sensor and related controlling circuits.

BRIEF DESCRIPTION OF THE DRAWINGS

Table 1 is a list that identifies each of all the 27 tested chemicals using the presently invented device.

Table 2 is a list that defines each of the average measured values, standard deviation, response time and recovery time of some tested chemicals using the presently invented device.

DETAILED DESCRIPTION

Figure 2:
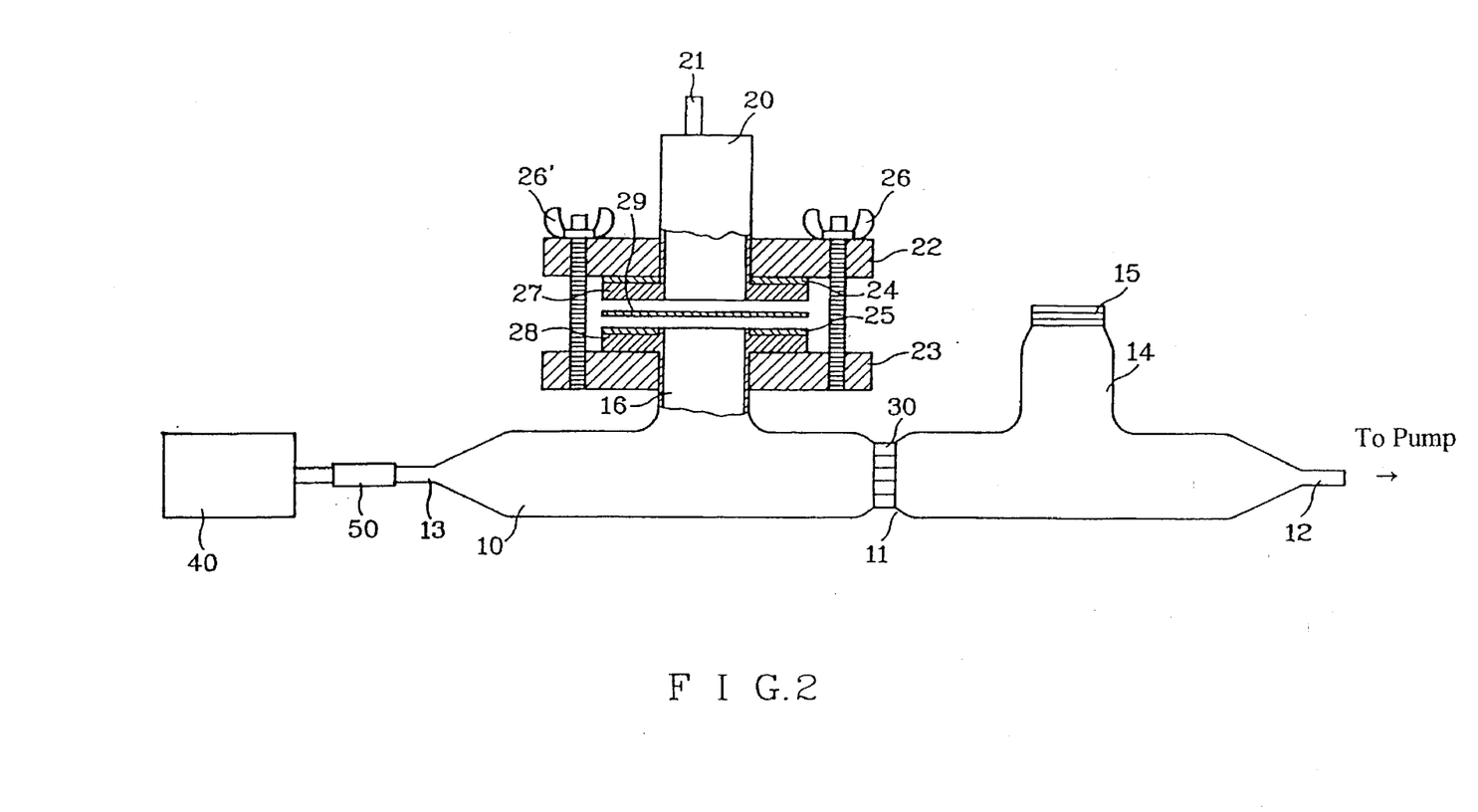
FIG. 2 is the side view of the presently invented device.
Figure 3:
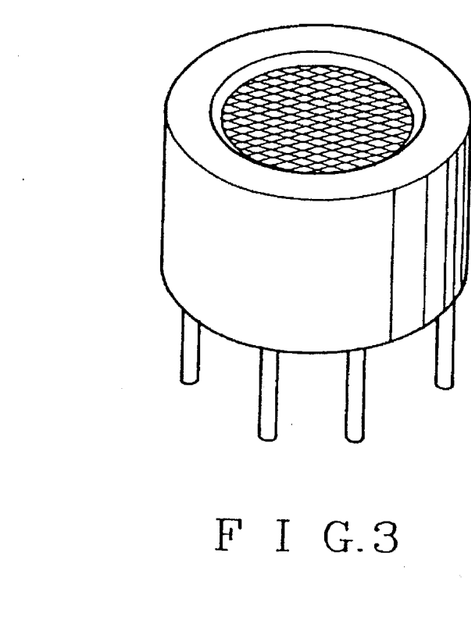
FIG. 3 is the perspective view of the sensor component of this invented device.

FIG. 2 is a side view of the presently invented device. It comprises mainly a test chamber (10), a sample cup for the solvent (20), a gas diffusing pan (30), an air filtering apparatus (40), etc. The test chamber (10) is substantially a round tube, of which both ends are tapered. The rear end of the aforesaid tube is a gas outlet (12), while the front end is an air inlet (13). The aforesaid gas diffusing pan (30) is accommodated in a groove (11), which locates in the middle portion of the test chamber (10). On the top of its front section a testing port (16) is located, which is a beetle cylinder with a flange (28) of a lager diameter on its top. A bulged cylinder (14) for accommodating the sensor (60), as shown in FIG. 3, is located on the top of the rear section of the test chamber (10). The top end of the bulged cylinder (14) is tailored with screw threads (15) for connecting with the cap (not shown in FIG. 3) of the sensor (60). The solvent sample cup (20) in a hollow cylindrical shape is mounted on the top of the testing port (16) of the test chamber (10). A flange (27) of the identical size as the aforesaid flange (28) is mounted on the bottom of the solvent sample cup (20). By connecting both flanges (27), (28) with the upper and lower fixing plates (22), (23) the sample cup (20) is joined with the testing port (16). The upper and lower fixing plates (22), (23) have lower and upper surfaces on the bottom and top thereof that are covered on the top and bottom of the flange (27) and flange (28), respectively. Both upper and lower fixing plates (22), (23) are implemented with four screw holes, respectively, permitting four long screws (26) to adjoin the solvent sample cup (20) and the testing port (16) of the test chamber (10) tightly. An upper gasket (24) is put between the upper fixing plate (22) and the flange (27) on the bottom of the solvent sample cup (20). A lower gasket (25) is then placed between the tested sample (29) and the flange (28) of the testing port (16). In the present invention the upper and low fixing plates (22), (23) are made of Teflon, and the upper and lower gaskets (24), (25) are made of silicon rubber, which can prevent the leakage of liquid from the gap. The tested solvent can be poured into the solvent sample cup (20) via the opening (21) with a smaller diameter located on the top of the aforesaid sample cup (20).

Figure 4:
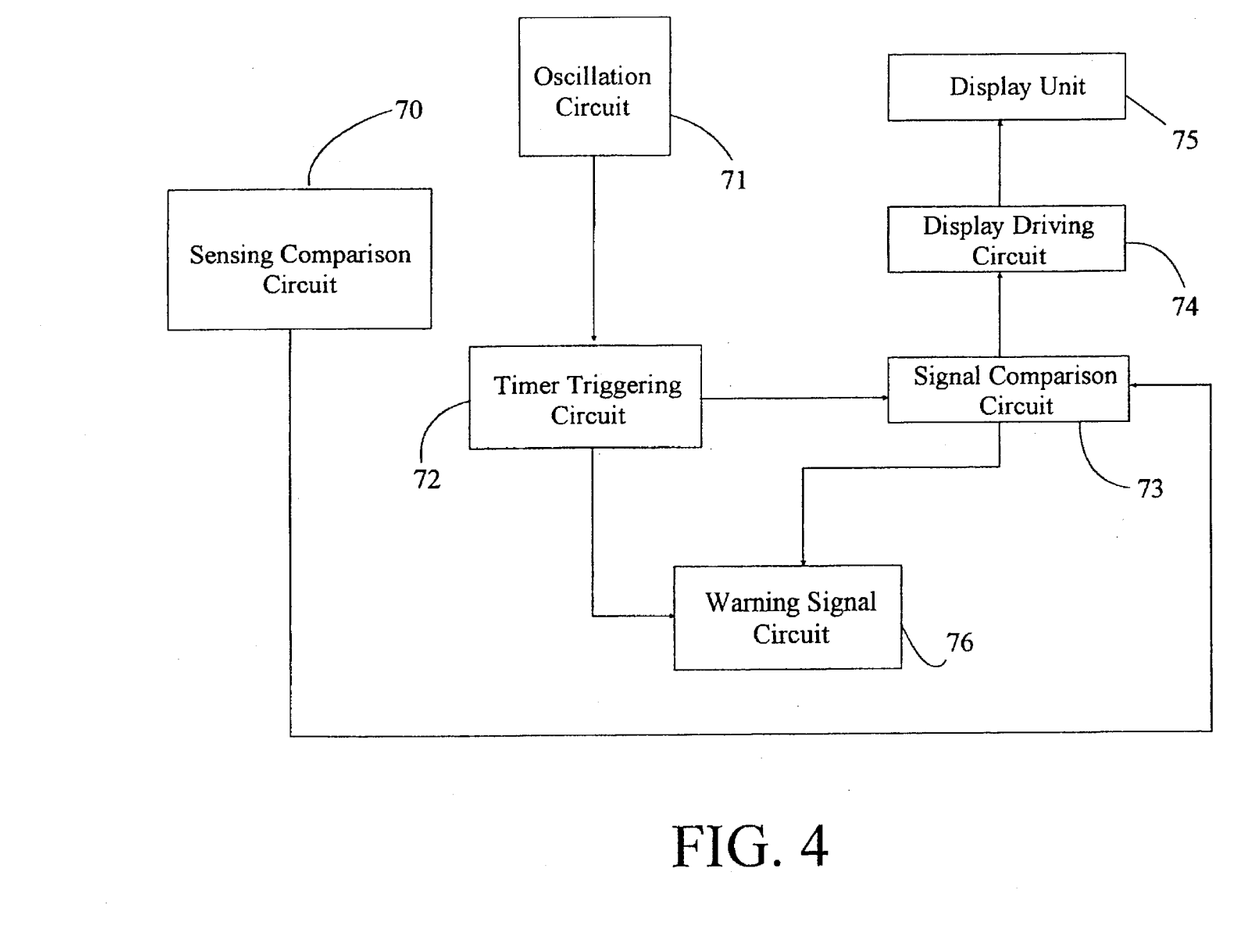
FIG. 4 is the block diagram of the control circuit for the sensor display of this invented device.
Figure 5:
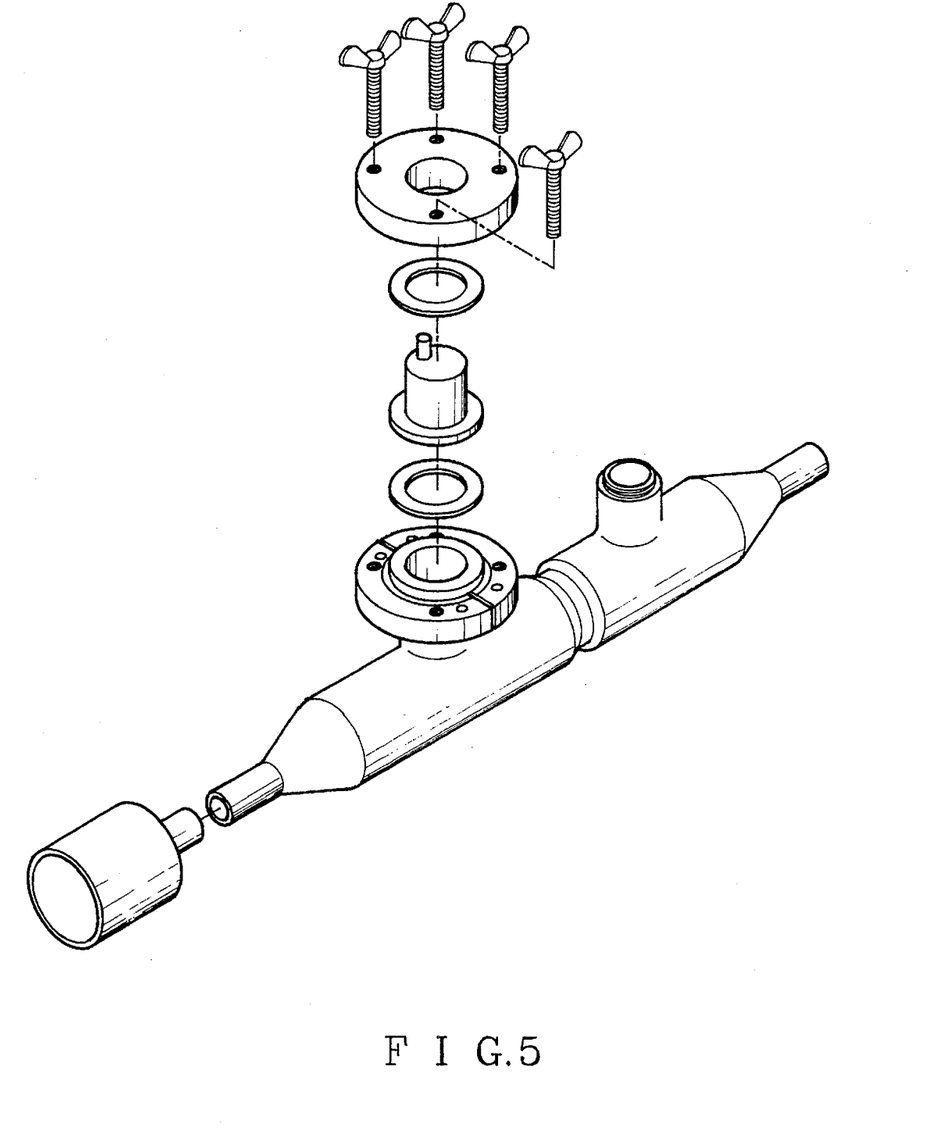
FIG. 5 is a disassembled stereograph of the present invention.

An air filtering apparatus (40), containing active carbon to filtrate flowing air from exterior, is connected to the test chamber (10) via a rubber tube (50). The gas sensing component (60) utilized in this invented device is a semiconducting type of metal oxide sensor. The perspective view of the aforesaid component (60) is shown in FIG. 3. A circuit is appropriately constructed to control the gas sensing component (60) for converting the acquired data from the aforesaid gas sensor to digital electronic signals. The variation of gas concentration is detected by the aforesaid gas sensor, which converts the data to the signals of voltage output in a linear manner where accessory integrated electronics performs such alteration conformably. FIG. 4 shows the circuit block diagram for the sensing-and-display control of the present invention. The signals detected by the aforesaid gas sensing component (40) of semiconducting type of metal oxide are compared with pre-set values and then the time is displayed. As soon as the gas concentration reaches the pre-set value, a warning signal is sent out to inform users. The aforesaid circuit comprises a sensing comparison circuit (70), an oscillation circuit (71), which is connected to a timer triggering circuit (72), and then connected to the signal comparison circuit (73), display driving circuit (74) and display unit (75), alternately. The input of the warning signal circuit (76) is connected with the signal comparison circuit (73) and timer triggering circuit (72) to constitute the warning function.

The operation of the control circuit is described below: The pre-set concentration value is a pre-determined voltage value as stored in an electronic memory built in the signal comparison circuit. This pre-determined voltage value is obtained beforehand when the gas sensor is in contact with the tested solvent during preliminary sensor exposure trails/calibrations. When the circuit is turned on, the timer is started. As soon as the detected solvent concentration is higher than the pre-set value, i.e., the measured voltage by the gas sensor is larger than the pre-determined voltage value, the timer stops and the time limit is shown on the display unit, in the meanwhile, the warning signal is sent out to inform users.

The test process of the presently invented device is described as follows: During the test the air filtering apparatus (40) containing active carbon filtrates the input of flowing air. The gas outlet (12) in the rear end of the test chamber (10) is attached with a pump (the flow rate is about 150 ml/min) to draw the air in the test chamber (10). The tested sample (29) is placed in the conjunction between the testing port (16) on the test chamber (10) and the solvent sample cup (20), i.e., between the flange (27) of the sample cup (20) and lower gasket (25). The four long screws (26) are used to tighten the upper and lower fixing plates (22), (23) and force the two flanges (27), (28) to firmly clamp the tested sample (29) together. Then the tested solvent is poured into the solvent sample cup (20) via the opening (21), and the circuit is turned on, and at the same time the timer is triggered for time counting. The pre-set concentration value is pre-determined and the pump begins to draw air from the test chamber (10). At the very beginning, the tested solvent would not permeate through the tested sample (29), but it permeates therein after a period of time. Under the operation of the aforesaid pump, gas diffuses uniformly by passing the gas diffusing pan (30), and allow the gas sensing component (60) in the rear portion of the test chamber to accurately detect the gas concentration of the tested solvent. When the detected value reaches the pre-determined concentration, it will show the tested specimen (29), e.g., gloves or protection wears, has lost its protection capability. At this time, the display unit indicates the time value showing the service life of this tested specimen (29) in the specific solvent. The tested specimen (29) herein is cut in a circular shape of with 4.7 cm diameter from gloves or protection wears. Hence, the service life of unknown gloves or protection wears in a specific solvent can be easily understood in the working area and avoid a lot of complicated procedures and methods.

Figure 6:
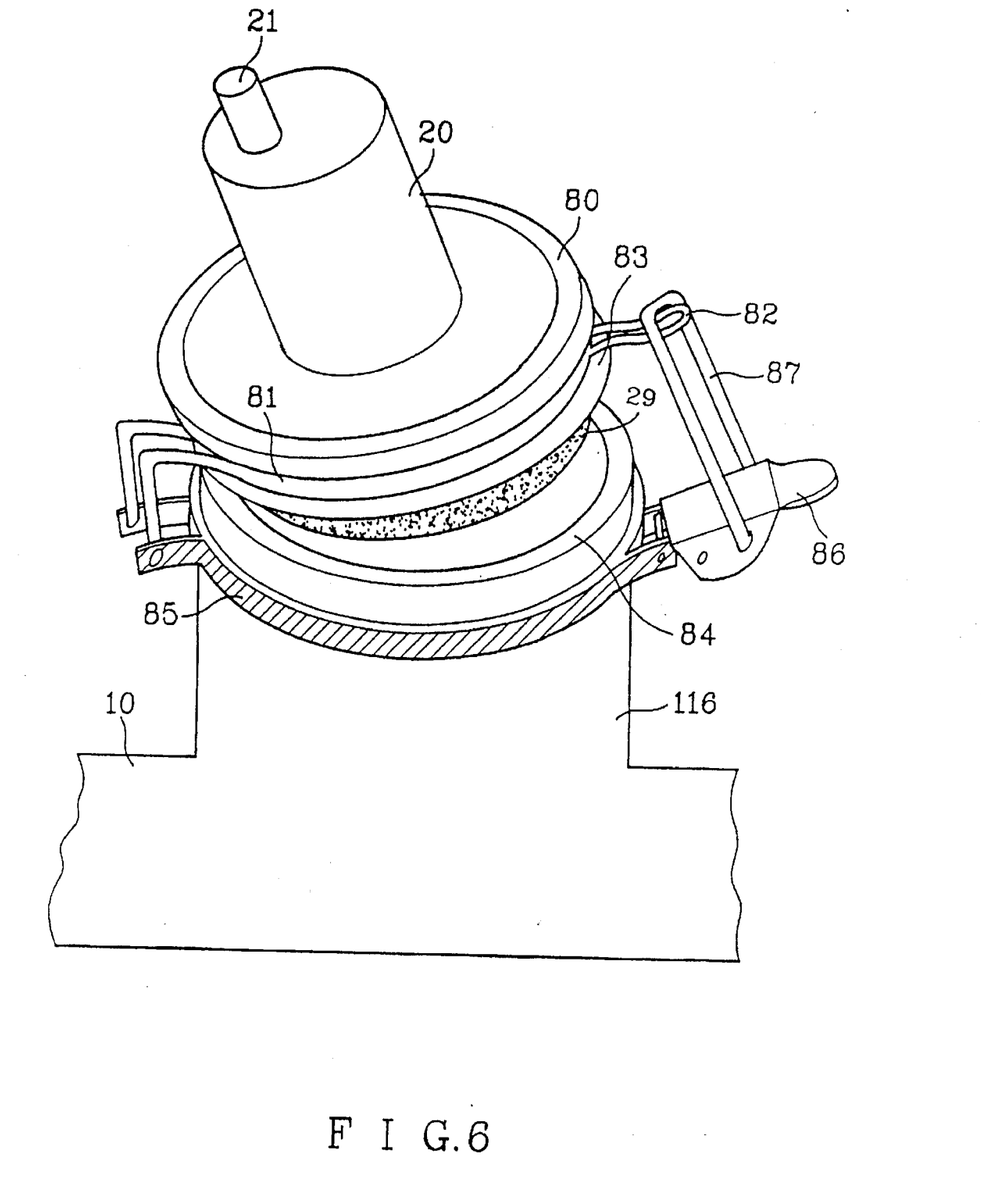
FIG. 6 is another perspective view of the presently invented device.

Another kind of connection can be used in the present invention, such as a normal jar seal of a traditional method, e.g., a clasp. This alternative applied method in this invention is shown in FIG. 6. An adhesion ring (84) is placed on the top end of the testing port (16) of the test chamber (10). Under the adhesion ring (84), a metal hoop (85) is used to tightly clamp the testing port (16). In the front end of the metal hoop (85) a clasping crank (86) with a clasping ring (87) is mounted. Another adhesion ring (80) is attached on the bottom of the solvent sample cup (20), and a metal ring (81) is mounted on a groove in the middle portion of the aforesaid adhesion ring (80). The rear end of the metal ring (81) is connected with the metal hoop (85) and its front end is joined with a metal hook (82), which retains the clasping ring (87). Under the adhesion ring (84), a gasket (83) is placed and enables a tight joint between the upper and lower adhesion rings (80), (84). During the test, place the tested specimen (29) between the gasket (83) and adhesion ring (84), engage the clasping ring (87) with the metal hook (82), and then push down the clasping crank (86), permitting a tight joint between the upper and lower adhesion rings (80), (84). The following test procedures are the same as the aforementioned setup in the previous section, therefore no further description is given herein.

Figure 7:
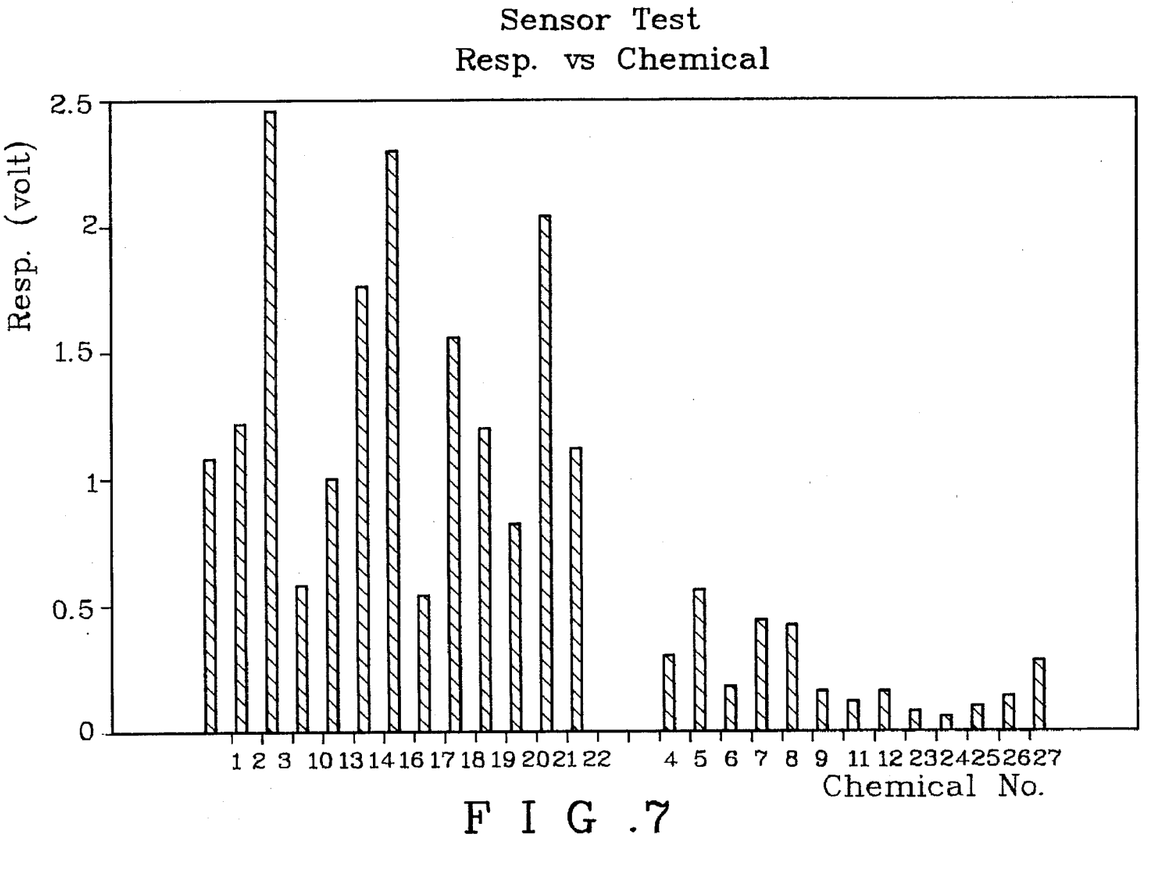
FIG. 7 shows the average detected voltage value of sensor response to different kinds of chemicals using the presently invented device.
Figure 8:
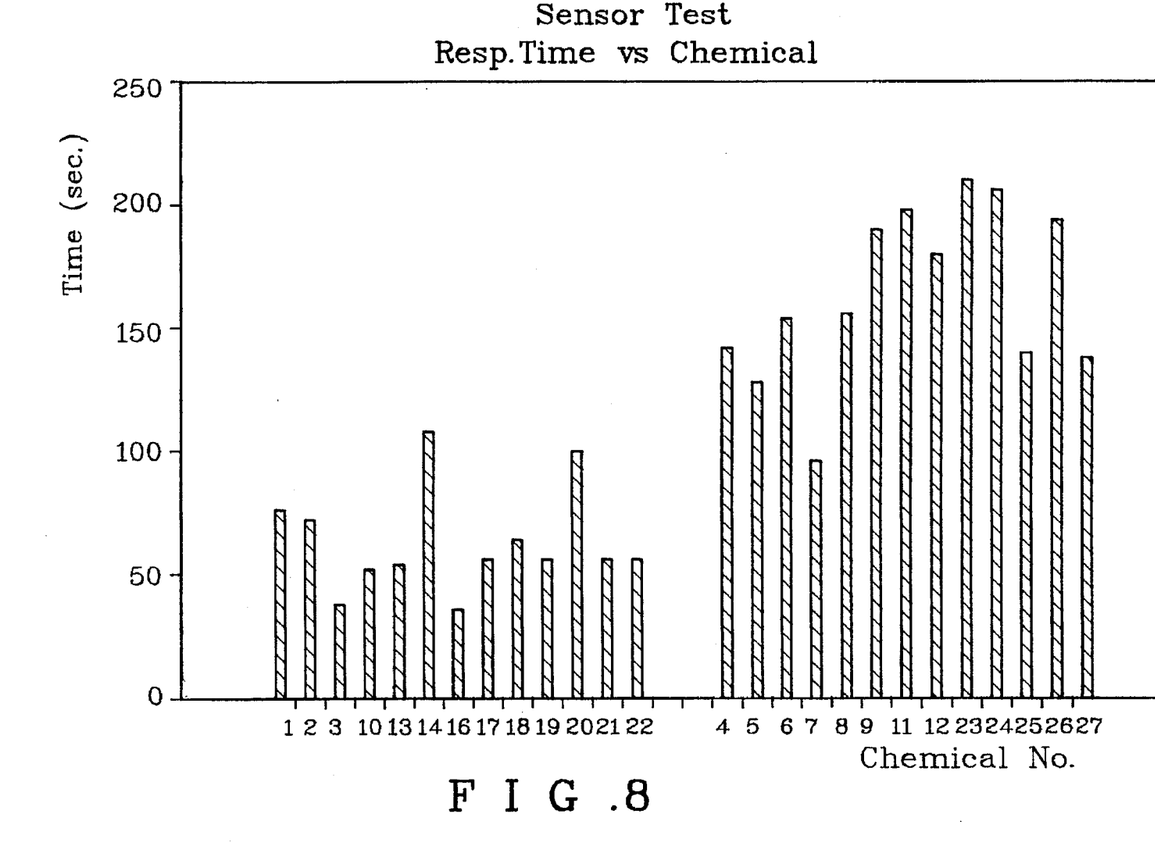
FIG. 8 shows the average response time (T90) of sensor response to 27 kinds of chemicals using the presently invented device.
Figure 9:
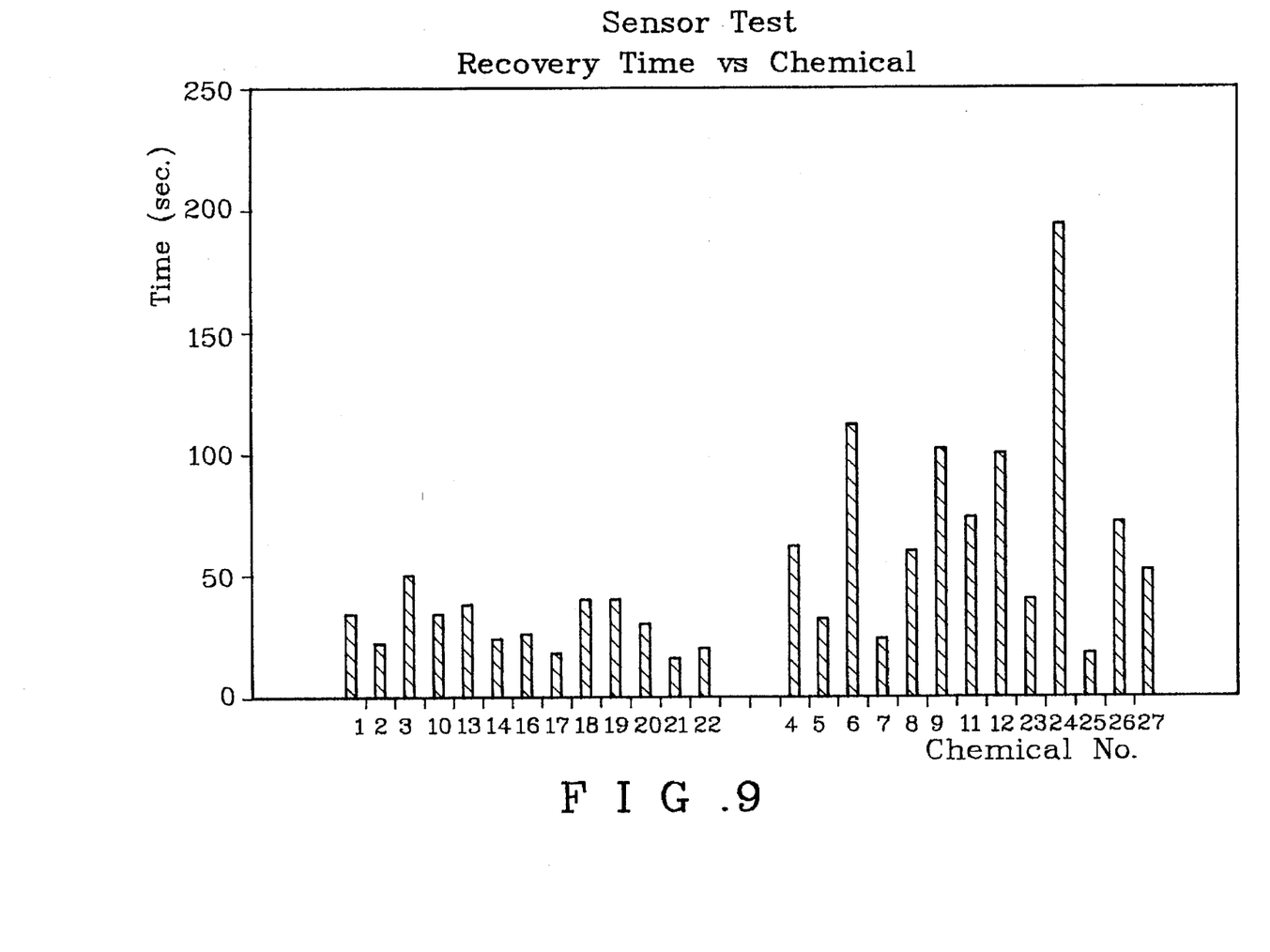
FIG. 9 shows the average recovery time (R30) of sensor response after exposure to any of 27 kinds of chemicals using the presently invented device.

Moreover, the presently invented device has been used to test 28 kinds of chemicals. The tested results are illustrated as follow:

Table 1 lists the 27 tested chemicals. An average value and a standard deviation were calculated (as shown in FIG. 7) according to 15 measured values, which were detected by five sensors under three tests. A curve of average values of the detected values for each test was obtained along with the maximum measured value of sensor voltage output e. In the first phase of the experiment, 18 kinds of chemicals, namely, 1, 2, 3, 4, 5, 9, 10, 11, 12, 13, 14, 16, 17, 18, 21, 26, and 28 were tested. In the second phase of the experiment, 12 kinds of chemicals, namely, 1, 6, 8, 9-1, 12, 15, 16, 19, 20, 22, 24, and 25, were tested. The chemicals of number 1, 12, and 16 were tested again in the second phase of the experiment, because there was a two-month time difference between these two experiments. The tested data of the second phase experiment were generally lower than that of the first phase experiment. The test results of 13-3 (the third test of the toluene in the first phase experiment) and 22-6 (the third test of iso-pentyl alcohol in the second phase experiment) were abandoned since the circuits were out of order for the first sensor and forth sensor during the tests, respectively. In addition, during the first phase experiment, chemical 28, sulfuric acid, was unable to vaporize completely in the sample container, which means the concentration of sulfuric acid could not reach 4000 ppm, i.e., the detected concentration by the sensor did not reach 8 ppm. Nevertheless, the three test results were still taken into account. Due to the aforesaid experience, chemical 27, sodium hydroxide (50%) was not tested. The two gases, number 27, hydrogen chloride, and number 23, methyl chloride, were unavailable in the lab, so that they were not tested. ach test was considered at the four-minute point of the aforesaid curve. The time (t90) can be located on these curves of 90% of the maximum value. The average response time (T90), as shown in FIG. 8, denotes the mean value of three t90 in three different tests using the same chemical. The recovery time (R30) is the average of three detected values of recovery times measured for the tests, in which the sensors were removed from the glass containers and placed in air and the time noted before the detected values drop to 30% (r30) of the maximum values. All the 30 tested chemicals can be divided into two groups according to the results of Table 4, and FIGS. 7, 8, and 9. The criteria is that (1) the average detected values is lager or less than 0.8 volt, (2) the response time (T90) is less than 90 seconds or not, and (3) the recovery time (R30) is less than 60 seconds or not. This can be used as a guidance to determine whether the specific sensor is suitable for the chemicals to be tested for gas permeation through a protective glove, garment, or skin covering articles and other personal barrier wears.

In brief, the presently invented device provides an effective, fast, and accurate method to perform a measurement for various chemical protection gloves or wears in different kinds of solvent or their mixture in operation sites. Therein, the service life of gloves or protection wears in a specific solvent is known in advance. It would avoid any injury to users that is caused by the unawareness of malfunction of wears and gloves, and enhance the safety of using the protection wears for users.

TABLE 2

Tested Average Value,
Standard Tolerance Reaction Time and Recovery Time

| Compound Number | AVG | SD | T90 | R30 |
|---|---|---|---|---|
| 1 | 1.08 | 0.09 | 77 | 35 |
| 2 | 1.20 | 0.09 | 72 | 22 |
| 3 | 2.45 | 0.39 | 39 | 52 |
| 10 | 0.57 | 0.07 | 52 | 14 |
| 13 | 0.99 | 0.13 | 54 | 39 |
| 14 | 1.75 | 0.16 | 109 | 24 |
| 16 | 2.26 | 0.27 | 37 | 27 |
| 17 | 0.53 | 0.09 | 55 | 19 |
| 18 | 1.55 | 0.16 | 65 | 40 |
| 19 | 1.20 | 0.28 | 55 | 40 |
| 20 | 0.82 | 0.19 | 100 | 30 |
| 21 | 2.04 | 0.08 | 55 | 15 |
| 22 | 1.12 | 0.35 | 55 | 20 |
| 4 | 0.30 | 0.03 | 142 | 62 |
| 5 | 0.36 | 0.06 | 127 | 32 |
| 6 | 0.17 | 0.04 | 155 | 115 |
| 8 | 0.44 | 0.13 | 95 | 25 |
| 9 | 0.42 | 0.07 | 155 | 62 |
| 9.1 | 0.14 | 0.08 | 190 | 105 |
| 11 | 0.12 | 0.03 | 197 | 75 |
| 12 | 0.15 | 0.04 | 180 | 102 |
| 15 | −0.19 | 0.10 | 20 | 1280 |
| 24 | 0.08 | 0.03 | 210 | 40 |
| 25 | 0.04 | 0.02 | 205 | 200 |
| 26 | 0.09 | 0.02 | 140 | 19 |
| 28 | 0.13 | 0.03 | 194 | 74 |
| 29 | 0.27 | 0.08 | 139 | 52 |

What is claimed is:
1. A test device for testing chemical permeation of a tested sample comprising:
a test chamber, a solvent sample cup, a gas diffusing pan, an air filtering apparatus a gas sensitive sensor, means

TABLE 1

27 kinds of chemicals tested

| No. | Class | Chemical name | Phase | CAS NO. | D(g/mL) | Mol wt | LV (uL) |
|---|---|---|---|---|---|---|---|
| 1 | ketones | acetone | L* | 67-64-1 | 0.79 | 58.08 | 6.02 |
| 2 | ketones | methyl ethyl ketone | L | 78-93-3 | 0.81 | 72.10 | 7.27 |
| 3 | ketones | cyclohexanone | L | 108-94-1 | 0.94 | 98.20 | 8.53 |
| 4 | nitriles | acetonitrille | L* | 75-05-8 | 0.74 | 41.05 | 4.53 |
| 5 | nitriles | acrylonitrile | L | 107-13-1 | 0.81 | 53.10 | 5.35 |
| 6 | inorganic gases | ammonia (anhydrous) | G* | 7664-41-7 | 5000 ppm | 8 mL | |
| 7 | hydrocarbons | 1,3-dichloroethane | G* | 106-99-0 | 100% (1) | 4 mL (2) | 10 mL |
| 8 | hydrocarbons | 1,2-dichloroethane | L | 107-06-2 | 1.17 | 98.97 | 6.91 |
| 9 | hydrocarbons | 1,1-dichloroethane | L | 75-34-3 | 1.17 | 98.97 | 6.91 |
| 10 | hydrocarbons | m-xylene | L | 108-38-3 | 0.87 | 106.20 | 9.96 |
| 11 | hydrocarbons | n-heptane | L | 142-82-5 | 0.68 | 100.20 | 11.96 |
| 12 | hydrocarbons | n-hexane | L* | 108-88-3 | 0.66 | 86.17 | 10.69 |
| 13 | hydrocarbons | toluene | L* | 110-54-3 | 0.87 | 92.10 | 8.64 |
| 14 | sulfer cpds | carbon disulfide | L* | 75-15-0 | 1.26 | 76.10 | 4.93 |
| 15 | elements | chlorine | G* | 7782-50-5 | 9.81% | 400 uL | |
| 16 | amines | diethylamine | L* | 109-89-7 | 0.71 | 73.14 | 8.44 |
| 17 | amides | dimethylformamide | L* | 68-12-2 | 0.94 | 73.09 | 6.32 |
| 18 | esters | ethyl acetate | L* | 141-78-6 | 0.90 | 88.10 | 8.01 |
| 19 | esters | methyl acrylate | L | 96-33-3 | 0.96 | 86.10 | 7.32 |
| 20 | heterocyclic cpds | ethylene oxide | G* | 75-21-8 | 100% (1) | 4 mL (2) | 10 mL |
| 21 | hydroxylic cpds | methanol | L* | 67-56-1 | 0.79 | 32.10 | 3.32 |
| 22 | hydroxylic cpds | iso-pentyl alcohol | L | 123-51-3 | 0.81 | 88.20 | 8.89 |
| 23 | halogen cpds | methylene chloride | L* | 75-09-2 | 1.31 | 84.94 | 5.29 |
| 24 | halogen cpds | tetrachlorethylene | L* | 127-18-4 | 1.62 | 165.80 | 8.35 |
| 25 | nitro cpds | nitrobezene | L* | 98-95-3 | 1.21 | 123.10 | 8.30 |
| 26 | inorganic acids | sulfuric acid (conc.) | L* | 7664-93-9 | 1.84 | 98.08 | 4.35 |
| 27 | ethers | tetrahydrofuran | L* | 109-99-9 | 0.89 | 72.10 | 6.62 |

*ASTM F1001-89 LIST OF CHEMICALS for measuring elapsed time, double gasket sealing means and twin fixing plates with multiple screw fastening mechanism; the front end of said test chamber is an air inlet and is connected to said air filtering apparatus via a rubber tube, while its rear end is a gas outlet and is connected to a pump for drawing air; said gas diffusing pan is accommodated in a groove located in the middle portion of said testing chamber; a bulged cylinder for accommodating the sensor is located on the top of the rear section of said testing chamber; on the top of its front section a testing port is located, which is a beetle cylinder with a testing port top flange; the solvent sample cup is a hollow cylinder with a smaller opening on its top end for admission of solvent poured thereinto, and a sample cup bottom flange on its bottom end; the aforesaid sample cup bottom flange is connected with said test port top flange of said testing port; connecting both flanges with an upper and lower fixing plate and two interface intervening gaskets by four screws, said solvent sample cup is joined with said testing port; said upper and lower fixing plates have lower and upper surfaces on the bottom and top thereof that are covered on the top and bottom of both said flanges, respectively; said upper gasket is put between said upper fixing plate and said cup bottom flange on the bottom of said solvent sample cup said lower gasket is then located between the tested sample and said test port top flange of the testing port; both upper and lower fixing plates are connected by four long screws and adjoin said solvent sample cup and said testing port of the testing chamber tightly; during the test, the aforesaid pump connected to the rear end of the said test chamber draws air; the active carbon is used for filtering air from the gas inlet located in the front end of said testing chamber; the tested specimen is placed between said flange of said solvent sample cup and said lower gasket, and is held tightly by fastening and tightening said upper and lower fixing plate using screws inserted through holes disposed therethrough; the tested solvent can be poured into the said solvent sample cup via the top opening; the aforesaid setup with a gas sensor, a display and control circuit can inform a testing technician of the service life of the tested specimen in a specific solvent by measuring an exposure time before soluble gas or fluid from said tested solvent permeates through said tested sample to produce a detectable gas concentration at said gas sensor.

2. A test device for testing chemical permeation as claimed in claim 1, wherein said gas sensor comprises a sensor component formed of a semiconducting metal oxide and is used as the sensing device of any gas concentration that permeates through said tested sample.

3. A test device for testing chemical permeation as claimed in claim 1, wherein said the display-control circuit is designed to be used with said semiconducting metal oxide sensor; a sensing comparison circuit, an oscillation circuit, and a timer triggering circuit are connected together, and then alternately linked to a signal comparison circuit, display driving circuit and a display unit; a warning signal circuit whose input is connected with said timer triggering circuit and whose output is connected to said signal comparison circuit; when a tested concentration reaches a pre-set value, a warning signal is sent out; said pre-set value of concentration is a pre-determined voltage in said signal comparison circuit; and said predetermined voltage is obtained when the gas sensing apparatus directly contacts the tested solvent in advance.

4. A test device for testing chemical permeation as claimed in claim 1, wherein the structure of the mated connection between said test chamber and said solvent sample cup is adopted from the design of a normal jar seal of a traditional clasping method; a first or upper adhesion ring is placed on the top end of said testing port of said test chamber; under said first adhesion ring, a metal hoop is used to tightly clamp said testing port around its circumferential wall; in the front end of said metal hoop a clasping crank equipped with a swingable clasping ring is mounted thereon; a second or lower adhesion ring is attached on the bottom of said solvent sample cup, and a metal ring is mounted on a groove in the middle portion of the said second adhesion ring; the rear end of said metal ring is pivotably connected with a support bracket on said metal hoop and its front end is fixedly attached and equipped with a metal protruding hook, which contacts, catches and retains said clasping ring when said clasping ring is swung upward towards said protruding hook in a proper manner when said clasping crank is pushed down, the upper and lower adhesion rings are tightly joined together; under said second or lower adhesion ring of said solvent sample cup, a gasket is placed and enables a tight joint between the upper and lower adhesion rings, which contains said tested sample disposed therebetween with an airtight seal at said mated connection effected by closure of said clasping crank under such clasping crank pressure.

* * * * *